(12) United States Patent
Grossinger et al.

(10) Patent No.: US 9,518,864 B2
(45) Date of Patent: Dec. 13, 2016

(54) CONTROLLABLE OPTICAL SENSING

(71) Applicant: Oculus VR, LLC, Menlo Park, CA (US)

(72) Inventors: Nadav Grossinger, Karmei Yosef (IL); Nitay Romano, Geva Binyamin (IL); Arnon Gratch, Tel Aviv (IL)

(73) Assignee: Facebook, Inc., Menlo Park, CA (US)

( * ) Notice: Subject to any disclaimer, the term of this patent is extended or adjusted under 35 U.S.C. 154(b) by 318 days.

(21) Appl. No.: 14/364,727

(22) PCT Filed: Dec. 13, 2012

(86) PCT No.: PCT/IL2012/050523
§ 371 (c)(1),
(2) Date: Jun. 12, 2014

(87) PCT Pub. No.: WO2013/088442
PCT Pub. Date: Jun. 20, 2013

(65) Prior Publication Data
US 2014/0346334 A1    Nov. 27, 2014

Related U.S. Application Data

(60) Provisional application No. 61/570,858, filed on Dec. 15, 2011.

(51) Int. Cl.
| | |
|---|---|
| *G01N 21/55* | (2014.01) |
| *G01J 1/04* | (2006.01) |
| *G01S 17/46* | (2006.01) |
| *G01B 11/25* | (2006.01) |
| *G01S 7/481* | (2006.01) |

(Continued)

(52) U.S. Cl.
CPC .............. *G01J 1/0411* (2013.01); *G01B 11/25* (2013.01); *G01J 1/044* (2013.01); *G01J 1/0448* (2013.01); *G01N 21/55* (2013.01); *G01S 7/4814* (2013.01); *G01S 17/46* (2013.01); *G02B 3/10* (2013.01); *G02B 5/1876* (2013.01);

(Continued)

(58) Field of Classification Search
CPC ........ G01S 17/46; G01S 17/89; G01S 7/4814; G01B 11/25; G01N 21/55; G01J 1/044; G01J 4/0411; G01J 1/0448; G02B 27/58; G02B 27/4205; G02B 5/1876; G02B 3/10
See application file for complete search history.

(56) References Cited

U.S. PATENT DOCUMENTS 3,379,832 A * 4/1968 Judin ................ H04N 3/02
250/227.26
5,786,582 A * 7/1998 Roustaei ............ G03F 7/705
235/462.07

(Continued)

FOREIGN PATENT DOCUMENTS

DE    4115445 A1 *  1/1992
EP    2166305 A1 *  3/2010

*Primary Examiner* — John Lee
(74) *Attorney, Agent, or Firm* — Fenwick & West LLP

(57) ABSTRACT

An optical sensing device for using light to locate objects or features in a field of view comprises a light source; a controllable lens having two states and being controllable between them, for example a multifocal lens having two or more foci for focusing light from the light source; and a sensor able to sense light reflected from an object, to determine information of the object. The use of two or more foci adds dynamic range to optical sensing to allow for reliable detection over a wide range of distances.

12 Claims, 8 Drawing Sheets

(51) Int. Cl.
*G02B 3/10* (2006.01)
*G02B 5/18* (2006.01)
*G02B 27/42* (2006.01)
*G02B 27/58* (2006.01)
*G01S 17/89* (2006.01)

(52) U.S. Cl.
CPC ......... *G02B 27/4205* (2013.01); *G02B 27/58* (2013.01); *G01S 17/89* (2013.01)

(56) References Cited

U.S. PATENT DOCUMENTS

| | | | | |
|---|---|---|---|---|
| 6,040,910 A * | 3/2000 | Wu | G01B 11/2527 | 356/613 |
| 6,073,851 A * | 6/2000 | Olmstead | G06K 7/10702 | 235/454 |
| 6,295,168 B1 * | 9/2001 | Hoffnagle | G02B 13/18 | 359/691 |
| 6,825,992 B2 * | 11/2004 | Shuman | G02B 27/09 | 359/718 |
| 6,950,194 B2 * | 9/2005 | Sandstrom | G03F 9/7049 | 356/401 |
| 7,053,999 B2 * | 5/2006 | Goldberg | G01N 21/9501 | 356/237.4 |
| 7,619,735 B2 * | 11/2009 | Milshtein | G01N 21/8806 | 356/340 |
| 7,777,932 B2 * | 8/2010 | Zalevsky | G02B 27/0075 | 359/245 |
| 8,373,919 B2 * | 2/2013 | Foller | G03B 9/02 | 359/267 |
| 8,390,926 B2 * | 3/2013 | Bordenyuk | G01J 1/0214 | 359/385 |
| 8,415,607 B2 * | 4/2013 | Duerksen | H01L 31/1055 | 250/208.2 |
| 8,786,757 B2 * | 7/2014 | Shpunt | G02B 27/1066 | 348/336 |
| 8,844,823 B2 * | 9/2014 | Fritz | G06K 7/10633 | 235/462.33 |
| 2004/0004723 A1 * | 1/2004 | Seko | G01B 9/02 | 356/498 |
| 2004/0008349 A1 * | 1/2004 | Norton | G01J 3/02 | 356/369 |
| 2004/0246474 A1 * | 12/2004 | Guetta | G01N 21/8422 | 356/237.2 |
| 2005/0203492 A1 * | 9/2005 | Nguyen | A61F 9/008 | 606/4 |
| 2006/0012802 A1 * | 1/2006 | Shirley | G01B 11/2531 | 356/603 |
| 2007/0195662 A1 * | 8/2007 | Ando | G11B 7/0909 | 369/44.32 |
| 2008/0106746 A1 * | 5/2008 | Shpunt | G01B 11/2513 | 356/610 |
| 2008/0156577 A1 * | 7/2008 | Dietz | G10K 11/30 | 181/176 |
| 2009/0296064 A1 * | 12/2009 | Cobb | G03F 7/70091 | 355/71 |
| 2010/0039689 A1 * | 2/2010 | Sayag | G02B 5/005 | 359/241 |
| 2010/0073461 A1 * | 3/2010 | Hammes | F16P 3/14 | 348/42 |
| 2011/0128412 A1 * | 6/2011 | Milnes | G02B 27/22 | 348/231.99 |
| 2011/0158508 A1 * | 6/2011 | Shpunt | G01B 11/25 | 382/154 |
| 2011/0254998 A1 * | 10/2011 | Bourdon | H04N 5/243 | 348/362 |
| 2013/0163099 A1 * | 6/2013 | Liphardt | G02B 3/00 | 359/723 |
| 2013/0169966 A1 * | 7/2013 | Shchegrov | G01N 21/4738 | 356/369 |
| 2014/0346334 A1 * | 11/2014 | Grossinger | G01S 17/46 | 250/229 |

* cited by examiner

CONTROLLABLE OPTICAL SENSING

CROSS-REFERENCE TO RELATED APPLICATIONS

This application is a National Phase Application of PCT International Application No. PCT/IL2012/050523, International Filing Date Dec. 13, 2012, claiming priority of U.S. Provisional Patent Application No. 61/570,858, filed Dec. 15, 2011, both of which are hereby incorporated by reference.

FIELD AND BACKGROUND OF THE INVENTION

The present invention, in some embodiments thereof, relates to a controllable optical sensor and, more particularly, but not exclusively, to an apodized optical device which is controllable, in one example to provide defined patterns and in another example to provide an optical 3D device for determining and tracking the positions in three dimensional space of objects in view and/or determining their 3D structure, and in a third example for an optical beam expander.

Current methods for optical 3D sensing and motion tracking consist of mainly two technologies, time-of-flight (TOF) and structured illumination.

TOF uses a similar concept as in range finding technology, where a light pulse is illuminated towards an object surface (generally from an IR emitter) and photons reflected from the object surface are collected via a sensor, generally a unique CMOS sensor with a very high rate of acquired frames per second designed exclusively for these purposes. By measuring the time from the triggered light pulse until the reflected photons are received by the sensor, it is possible to calculate the distance and effectively the location in space of the object surface. By emitting and measuring multiple light pulses in many directions it is possible to extract a 3D mapping of the targeted space.

One limitation of this method is the inability to obtain depth sensing on objects at close proximity to the depth sensor. General operating ranges are known to be above one meter from the depth sensor. Thus gesture recognition for controlling the computer cannot be provided from a short distance, which is the distance a person normally uses a computer. Various techniques can be applied to overcome this limitation but they require additional methods and hardware components thus increasing the complexity of design and price.

An additional method for depth sensing comprises of illuminating the surface of an object with structured light, also known as a light pattern. The light is generally illuminated by an IR source emitting light through a diffractive optical element (DOE). A sensor located at some distance from the light source is used for collecting photons reflected from the object surface and by means of triangulation calculations, the distance from the surface is determined and a 3D mapping of the illuminated space is generated.

Gaming applications and the like, require a high 3D resolution of motion detection and tracking. In order to achieve the required resolution the projected structured light pattern is very dense. The density limits the method from operating in a full dynamic range of proximities. In order to effectively operate on distant objects the projected pattern is designed to appear dense. But when operating at close proximities, generally under 0.8 m, the projected features overlap and do not provide the pattern that is required for generating the necessary calculations for depth detection and motion tracking.

In order for structured light depth sensing of objects at a closer proximity range, it is possible to design a DOE such that the projected pattern is less dense at closer proximities. This design provides the required characteristics for discriminating between features of the projected pattern. For example, a random spots design that contains fewer spots allows for the separation between spots closer to the sensor. In these types of designs however, the resolution deteriorates throughout the distance since the spots diverge from each other, resulting in poor resolution at these larger distances.

Another option for discriminating between features is by using a lens with a relatively close focal point. However, in this type of setup the features at distant proximities are defocused, blurred and overlap, thus resulting in the same problems as with the first design but for distant proximity ranges.

Both of the mentioned methods are thus restricted to specific operating distances and no current method offers a solution for a single depth sensor to effectively operate on a full dynamic range of distances.

FIG. 1 illustrates a particular light pattern and an attempt to view it over a wide distance range. As can be seen in the images, the pattern features that are clear and discrete at a distance of 900 mm cannot be resolved at 300 mm and all that appears at 150 mm is a blur. Depth sensing cannot thus be performed at the smaller range using this system.

Other methods use various types of projectors to project images onto the object inspected in order to extract the 3D information. However, these types of imaging methods require an imaging lens to keep the image relatively in focus enabling the detection of the depth map around the focal plane of the projector. The need for focus again limits the dynamic range of operation of the device.

SUMMARY OF THE INVENTION

The present embodiments relate to dynamic control of an apodized lens to provide controllable beam patters for sensing. An example is sensing in 3D using multiple foci to allow for a large dynamic range of distances. Thus the apodized lens serves as a controllable multi-focal lens.

According to an aspect of some embodiments of the present invention there is provided an optical sensing device for using controllable light patterns to detect objects or features of the objects, the optical sensing device comprising:

a light source;

a controllable lens controllable between at least two states for focusing light from the light source into a space;

a sensor configured to sense focused light of the light source reflected from an object in the space to sense the object or the features of the object.

An embodiment may comprise a light structuring unit for adding structure to light of the light source, for recognition by the optical sensing device.

In an embodiment, the space is a three-dimensional space and the states are foci at two different distances.

In an embodiment, one of the foci is a focus at infinity.

In an embodiment, the light structuring unit is one member of the group consisting of a diffractive pattern generator, an amplitude mask, a phase mask, and a patterned film.

In an embodiment, the controllable lens comprises a lens surface shaped to provide an apodized surface function.

In an embodiment, the controllable lens is a diffractive lens having diffractive steps, each step having a height, and wherein respective heights are varied over the surface to provide the apodizing function.

An embodiment may comprise an adjustable shutter dynamically configurable to direct light controllably over the shaped surface to vary amounts of energy for respective foci.

In an embodiment, the controllable lens is a multi-focal lens having at least three foci.

In an embodiment, one of the foci is at infinity.

In an embodiment, the light structuring device is configured to structure the light such that light directed to different focal regions of the multi-focal lens are differentially structured for mutual recognition.

In an embodiment, the controllable lens is a multi-focal lens comprising a diffraction lens.

In an embodiment, at least one of the states is a beam expansion state.

According to a second aspect of the present invention there is provided an optical sensing method for using light to detect objects or features of objects in a field of view, the method comprising:

shining light from a light source on a controllable lens having at least two states for projecting light differentially from the light source into the field of view;

sensing focused light of the light source reflected from an object within the field of view to sense the object or features of the object.

In an embodiment, the controllable lens is a multi-focal lens controllable between at least two focal lengths.

In an embodiment, the controllable lens comprises a lens surface shaped to provide an apodized surface function.

In an embodiment, the controllable lens is a diffractive lens having diffractive steps, each step having a height, and wherein respective heights are varied over the surface to provide the apodizing function.

The method may comprise directing light controllably over the shaped surface to vary amounts of energy for respective foci.

The method may comprise directing light sequentially between different areas of the shaped surface.

In an embodiment, the controllable lens is a multi-focal lens having at least three foci.

The method may comprise structuring the light such that light directed to different focal regions of the multi-focal lens are differentially structured for mutual recognition.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS
OF THE INVENTION

The present invention, in some embodiments thereof, relates to an optical three-dimensional (3D) depth sensor and, more particularly, but not exclusively, to an optical 3D device for determining shapes and/or tracking the positions in three dimensional space of objects in view, and to a beam expander.

An embodiment is a depth imager device with extended dynamic range of its effective optical sensing, and comprises an image sensor, a light emitter projecting structured light at a predefined number of focal points and a processor able to process the resulting light patterns. Multi-focused structured light is projected into a view which includes an object of interest. The depth of the object is sensed by a structured illumination depth sensor which analyses the detected light structures that are in focus at the actual distance range of the object, the remaining light structures being out of focus.

Structured light may include a light pattern created by a laser or LED coupled with a diffractive pattern generator (phase mask), an amplitude mask, film or any type of imaging projector. The projector may be any kind of mirror that scans, whether based on one axis or two axes, a matrix of mirrors that can be switched individually, or a digital light processor (DLP)

Figure 1:
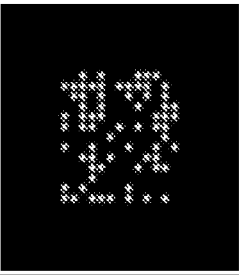
FIG. 1 is a tabular drawing showing a prior art system and illustrating the little dynamic range available.

For purposes of better understanding some embodiments of the present invention, as illustrated in FIGS. 2-10 of the drawings, reference is first made to the construction and operation of an optical 3D depth sensor whose results are illustrated in FIG. 1 for comparison at different depths. As shown the prior art system manages a clear and crisp result at 900 mm but at 300 mm the dots are barely resolved and at 150 mm the pattern is completely blurred.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 2:
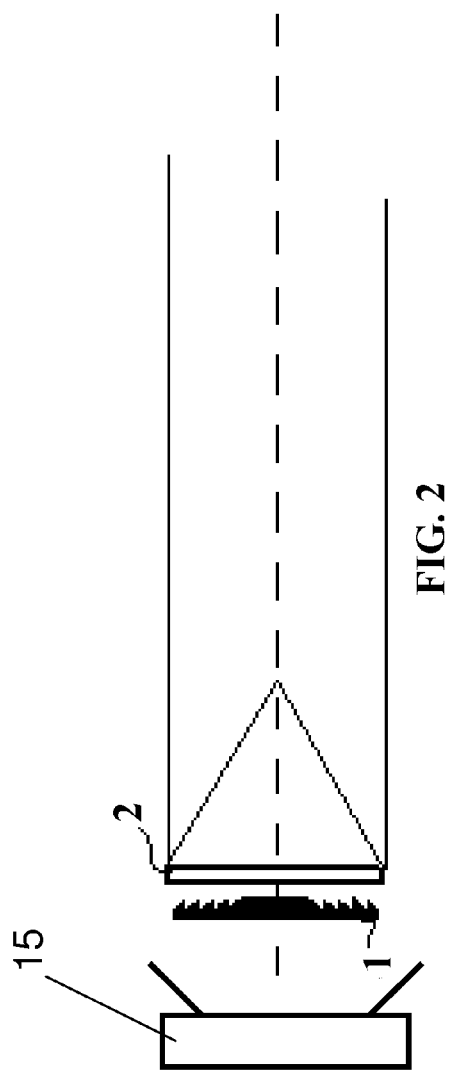
FIG. 2 is a simplified schematic diagram showing an embodiment of the present invention in which a diffractive lens and a patterning element provide structured light at a near focus and at infinity.

Referring now to the drawings, FIG. 2 illustrates a simplified device according to an embodiment of the present invention for using controllable light patterns to detect objects or features of objects in a field of view. A light source 15 shines light onto a controllable lens 1 which is controllable between two or more states for focusing light from the light source into the field of view. As shown, the two states are two different focal lengths, but they may also be two different patterns etc. A sensor (typically co-located with the light source 15) senses focused light of the light source reflected from an object in the field of view to sense the object or features of the object.

In an embodiment, the field of view may be a three-dimensional space and the two states may be two different focal lengths, possibly including one focus at infinity.

In an embodiment, one or more of the states may be a beam expansion state.

The use of a multi-focal lens may provide a cost effective method for expanding the dynamic range of a structured illumination based three-dimensional sensing system.

That is to say, a solution may provide a single three-dimensional optical sensor having an effective operational proximity ranging from several centimeters distance from the sensor to several meters. The projected pattern may be random or periodic and can be in any shape such as lines, spots, circles, ellipsoids or speckles, while the means of obtaining the desired pattern can be by use of a diffractive optical element (DOE) or by means of a mask or by any other suitable method.

In order to achieve separable features in the projected pattern at various distances, the controllable lens used may be a multi focal lens. The multi focal lens may focus the projected pattern onto two or more focal points with controlled relative energy distribution between them, as will be explained in greater detail below. In this way, the size of the features in the projected pattern may be minimized to a diffraction-limited spot size at two working distances simultaneously, but still allowing the resolvable separation needed for the depth sensing at each distance, thus allowing the system to operate over a wider dynamic range.

Focusing part of the light intensity to a specific focal point can cause a degradation of contrast at other focal points and distances. However, the light for the other depth, unfocused at the first depth, usually results in a relatively uniform background which does not prevent the identification of the pattern of the focused light, since the local intensity of the focused pattern is significantly higher.

The relative intensity of the projected pattern at each focal point may be defined at the design stage. The design may thus be made to achieve an optimized energy separation between the background noise which comes from other focal planes and the actual pattern in focus which is to be detected.

In a diffractive multi focal lens, the focal intensity ratio is determined by the depth of the diffractive steps. The following equation describes the relation between the diffractive step or tooth height and the relative focal intensity for a simple lens that focuses a portion of the light onto a single focus while the rest of the light propagates without focusing.

$$Eff = \frac{\sin(\pi*(1-\theta))}{\pi*(1-\theta)} \qquad \text{Equation 1}$$

θ=(n2−n1)*Δd
Δd=Etching depth.
n2—Refractive index of material.
n1—Refractive index of Environment. (for example air ≅1)

The optimal diffractive step height is determined based on the required dynamic range, number of focal points, complexity of the desired pattern, etc.

In addition, an apodized diffractive surface is presented. The apodized multi focal diffractive surface may consist of varying diffractive steps at heights which may achieve a dynamic energy distribution between focuses and thus a higher overall intensity, as will be explained in greater detail below.

An apodized lens is a focusing lens having a positive—concentrating—or negative-de-concentrating-power, that derives from a continuous spherical or aspherical profile. The lens profile may be flattened by phase wrapping modulo 2π and the current wavelength to achieve a flat diffractive surface having diffractive zones (teeth). The function of the lens after the 2π phase wrapping remains the same as the continuous profile before the modulus operation for the specific wavelength used. The height of the diffractive teeth can then be changed independently to alter the distribution of energy between the original focus of the diffractive profile, and the zero order which remains un-focused.

The optical power of the lens remains unchanged by the tooth-height alternation. Note that the apodized diffractive type of lens differs from a regular multi level diffractive element where a local change in height changes the optical function of the element.

An additional embodiment works by controlling the energy ratio between focuses using Liquid Crystal.

As can be seen from Equation 1 above, the efficiency distribution between focuses can be controlled by changing the difference in refractive indices, (n2−n1), in the same manner that it can be controlled by the diffractive height as described above.

Liquid crystal can change its refractive index properties by applying electrical voltage. Therefore a bi-layered element may be used in which the first layer consists of a diffractive lens with a diffractive pattern. A second layer of liquid crystal is applied on top of the diffractive surface in such a way that the liquid crystal fills the diffractive teeth. In this manner, if the refractive indexes of the liquid crystal and the diffractive element are equal, the combined element has no optical function and it acts like a window. If an electrical voltage is applied to the liquid crystal then the refractive index changes and the optical function of the diffractive surface becomes active. Therefore the voltage can be controlled to dynamically define the relative intensity values of the efficiency distribution between focuses.

The diffractive pattern may comprise a uniform depth between diffractive teeth or may be an apodized diffractive profile.

Additionally or alternatively, the liquid crystal can be separated to various zones on the diffractive element, for example ring zones, such that a different voltage can be applied to each of the zones separately. In this manner, each zone can contribute a different energy distribution to the focuses, creating a dynamic apodizing function.

A further embodiment uses the liquid crystal to change the diffractive pattern.

Liquid crystal can be used to change the pattern generation properties of the diffractive element completely. For example, a diffractive element can use two diffractive surfaces that create a phase function of the combination of the two surfaces. As described above, a liquid crystal layer can be applied on top of one of the diffractive layers. Changing the voltage applied to the liquid crystal can reveal or hide the diffractive optical function of the surface with the liquid crystal. Thus, the liquid crystal may be used to switch between the combined optical function of the surfaces on the one hand and the optical function of the single surface without the liquid crystal on the other hand.

One example of such a use is to apply a dense diffractive pattern for far working distances and a less dense diffractive pattern for closer distances. Changing between the two patterns can then be achieved merely as a result of applying a voltage.

Referring again to F the structure for illuminating the projected pattern through a bi-focal lens 1 is designed to project part of the light to a focal point at a close proximity to the illumination source. The lens 1 is shown as a diffractive lens having diffractive teeth. In the lens shown in FIG. 2 the teeth are all of the same height. A light structuring unit is provided by a DOE 2, which is designed to produce the desired pattern required for depth sensing calculations. In this manner, depth sensing of an object surface located at a more distant proximity is achieved by the known approach of using structured illumination and triangulation methods between identified parts of the structure. However a second nearer focal length allows for an additional set of structural features to be projected onto a nearer focus. The nearer set of structural features may be provided with a density more suitable for the nearer distance. By adding focused near proximity features at a near focus, the same depth sensor can discriminate between these features and perform the required processing for depth sensing at close proximities as well as at the greater distance, hence increasing the dynamic range.

Light may be provided by light source 15, which may be a source of white light or of coloured light at a particular wavelength including light from outside the visible spectrum such as IR or UV light.

Figure 3:
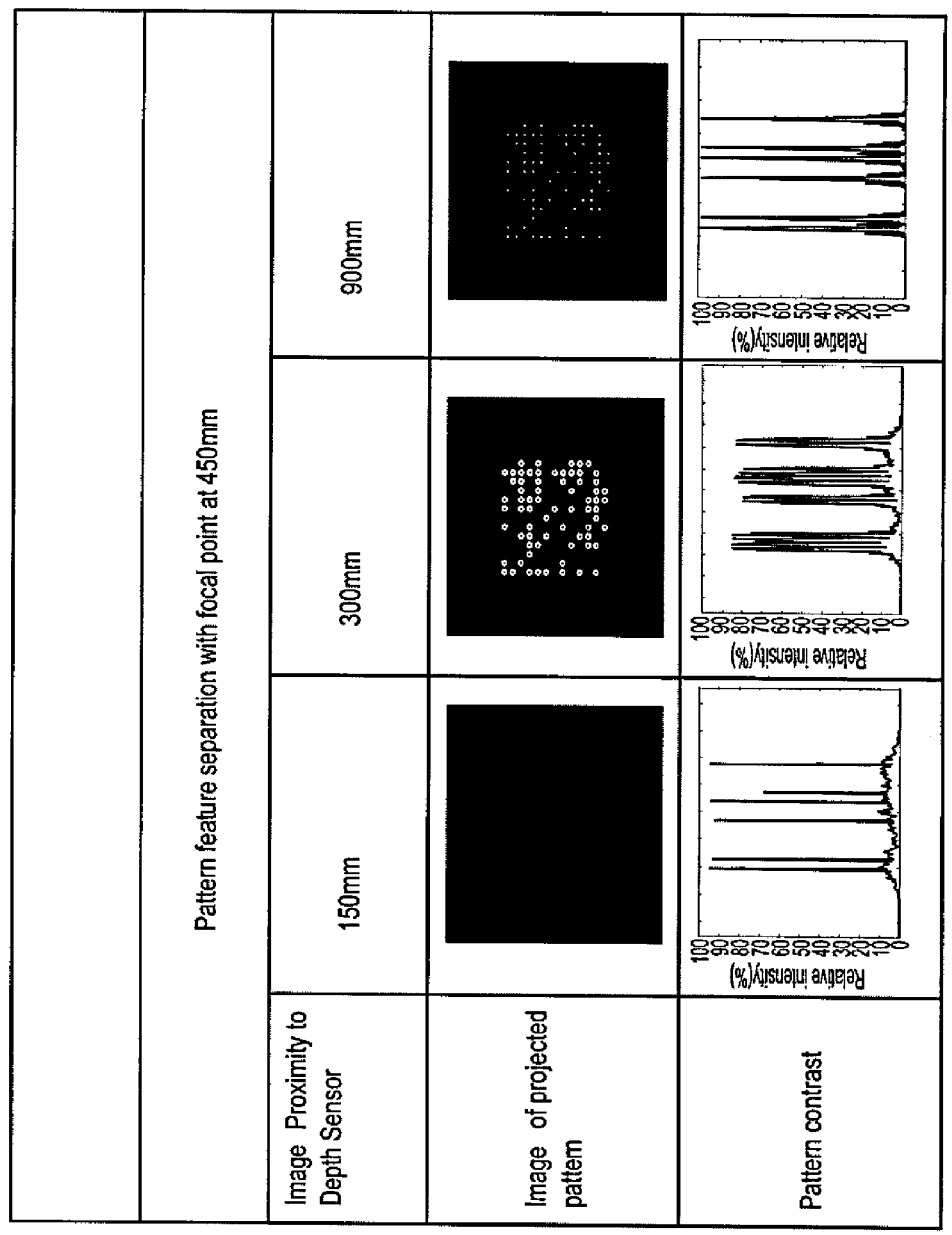
FIG. 3 is a tabular drawing showing the appearance of the structured light at various distances using the embodiment of FIG. 2.

Reference is now made to FIG. 3, which shows the results of carrying out the tests in FIG. 1 but on the bifocal arrangement of FIG. 2. FIG. 3 illustrates results obtained at the same distances as those shown in FIG. 1. The device shares a focus with that used for FIG. 1, but has a multi focal lens designed with an additional focal point at 450 mm. As can be seen in the images, the pattern features can be resolved easily at a distance of 300 mm, which the device used in FIG. 1 cannot do.

Figure 4:
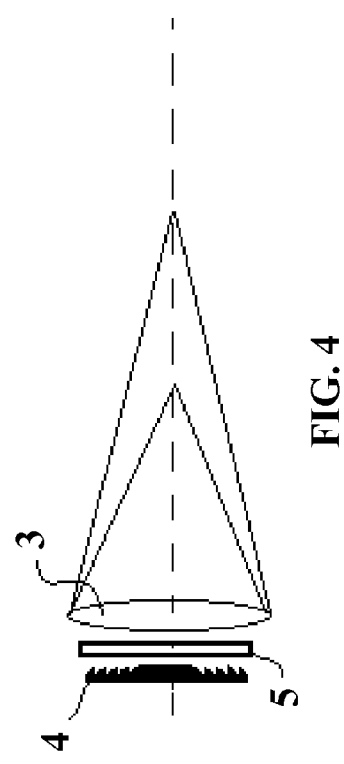
FIG. 4 is a simplified schematic diagram showing an embodiment of the present invention in which a diffractive lens, a patterning element and a refractive lens provide structured light at a near focus and at infinity.

Reference is now made to FIG. 4, which shows a structure for producing a second focal point of the projected pattern. The structure comprises a bi-focal lens 4, a refractive lens 3 and a pattern generating DOE 5, and has two near foci in addition to the focus at infinity.

An additional focal point may extend the flexibility of the pattern feature separation to a greater degree of pattern complexity. In addition, an extra focal point may give a softer transition between focal planes and may extend the dynamic range even more.

Figure 5:
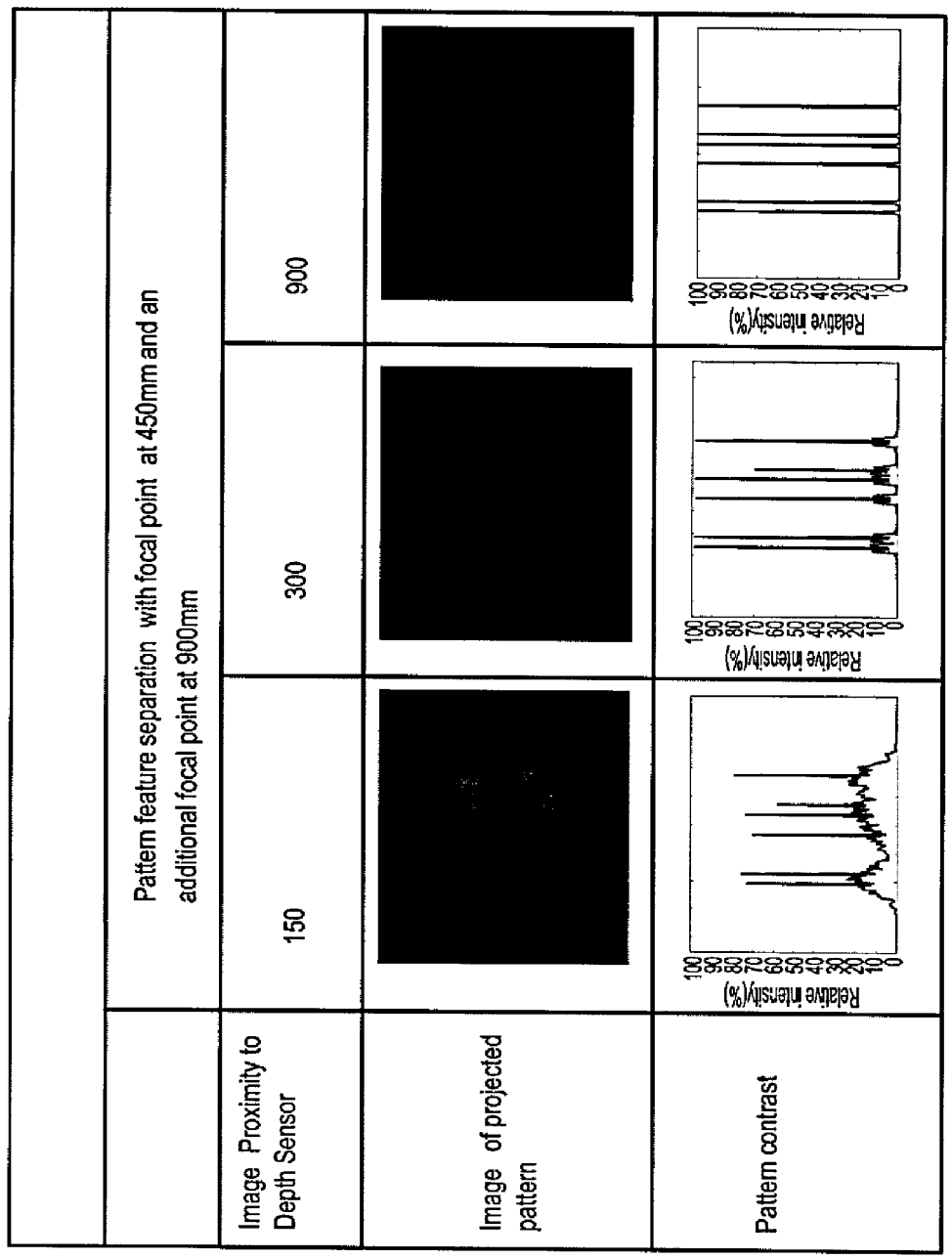
FIG. 5 is a tabular drawing showing the appearance of the structured light at various distances using the embodiment of FIG. 4.

FIG. 5 shows the same experiment as carried out in FIGS. 1 and 3, but with the device of FIG. 4. Specifically FIG. 5 illustrates results of detected light patterns from various distances with a multi focal lens designed with a second focal point at 450 mm and a third additional focal point at 900 mm.

Figure 6:
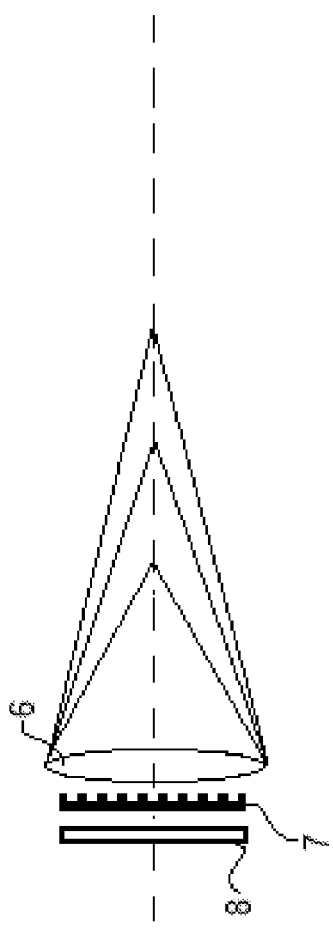
FIG. 6 is a simplified schematic diagram showing an embodiment of the present invention in which a diffractive lens, a patterning element and a refractive lens provide structured light at three separate foci.

Reference is now made to FIG. 6, which illustrates an optical structure for distributing the projected pattern to three foci-points. The light is passed through a pattern generator DOE 8, a binary multi focal lens 7 and a refractive lens 6. It is noted that here the third focus is obtained at some cost to the focus at infinity.

A regular projector may be used to produce the patterns.

Figure 7:
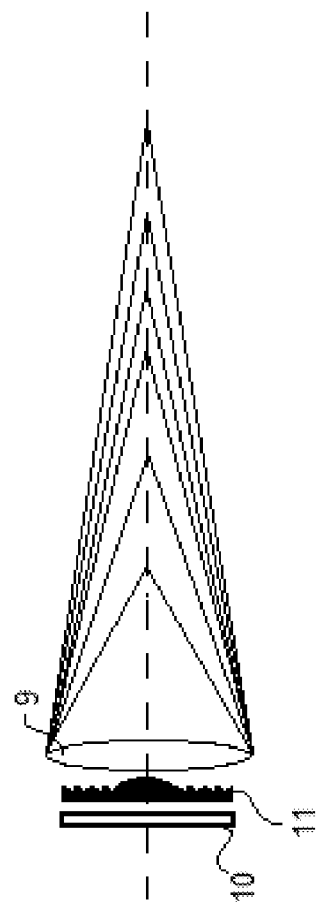
FIG. 7 is a simplified schematic diagram showing an embodiment of the present invention in which a diffractive lens, a patterning element and a refractive lens provide structured light at n separate foci, where n is illustrated as 6.

Reference is now made to FIG. 7 which illustrates a light path for distributing the projected pattern to N foci-points and comprises illuminating the light through a pattern generator DOE 10, a multi-focal lens 11 and a refractive lens 9. The embodiment of FIG. 7 is particularly useful where the light source is laser light.

Apodized Diffractive Multi Focal Lens:

Defining a fixed energy distribution between foci may not always achieve a clear pattern throughout the full required range of operation. For example, a complex pattern that is designed for a far operating distance may require relatively high intensity power in order to be detected by the camera. Applying the above mentioned method in order to achieve a high resolution at a near distance as well, may again require a higher relative intensity which in turn will interfere with the pattern at the far working distance. In each case there may be relatively large amounts of diffuse light intended for the other focus which interfere with pattern detection.

In order to solve this issue a method for dynamically changing the relative energy between the different focal lengths is provided. A multi focal lens with an apodized diffractive surface is provided. The apodized surface changes the height of each diffractive tooth or step based on an apodizing function. In this manner each diffractive zone contributes a different relative energy distribution to the various focuses defined. The apodized function can be determined flexibly to fit the requirements of the application.

The relative energy at the focuses is a direct function of the types of diffractive features that are exposed to the input light. As a result, the energy can be changed using a simple dynamic aperture or a beam expander setup. In other words the shutter can be altered to light different regions of the lens, thereby providing high energy where needed at any given time. The shutter could be set to wide aperture to illuminate the whole of the lens surface, or to a narrow aperture, to illuminate just the central portion of the lens. The shutter may be set to alternate between wide and narrow beams.

Figure 8:
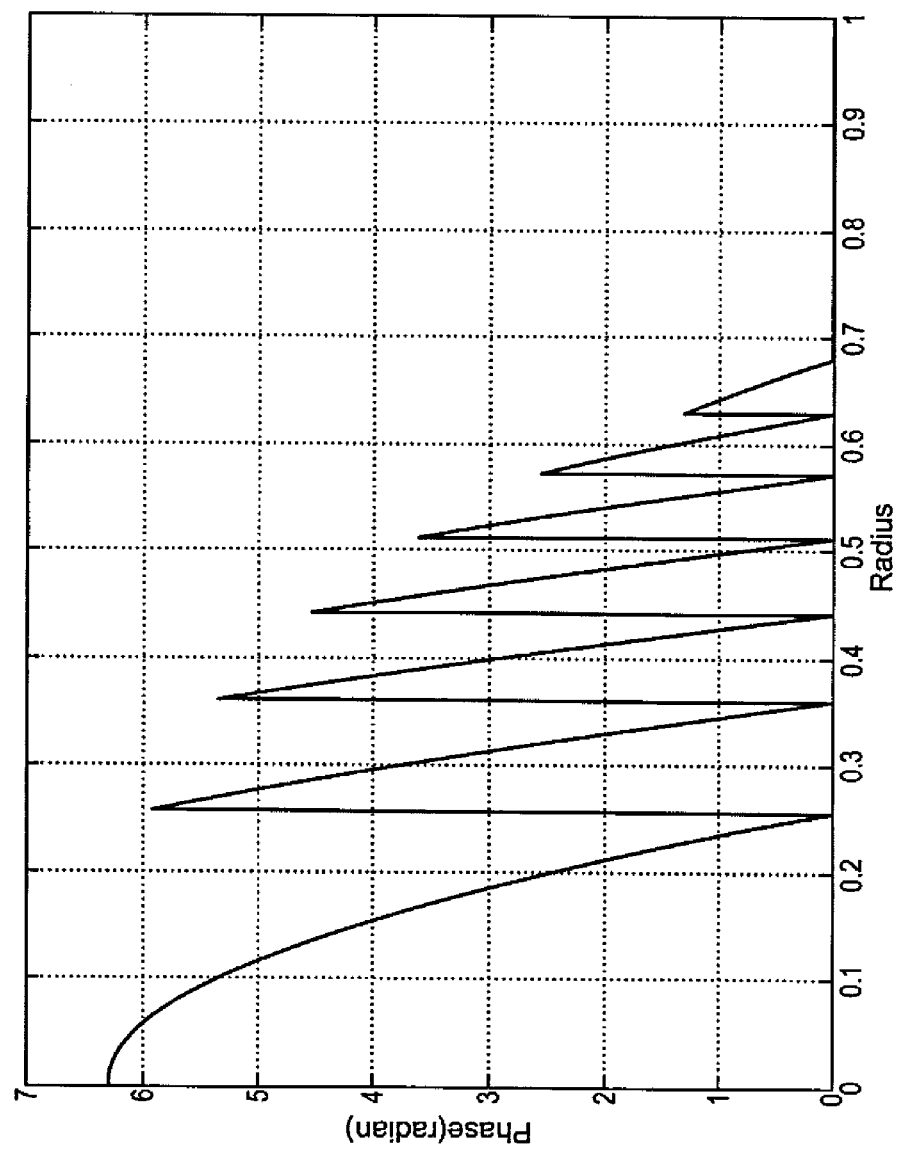
FIG. 8 is a simplified graph showing a function for an apodized lens.

Reference is now made to FIG. 8, which is a simplified graph illustrating a typical diffractive apodized surface function. In the apodized function shown, an additional optical power is added at smaller apertures/beam size, creating a clear pattern at the closer distance. Expanding the beam, on the other hand, may deliver higher efficiencies to the far distance image.

The apodized function can alternately be designed the opposite way, transferring the energy from the far to the near at larger beams/apertures.

Figure 9:
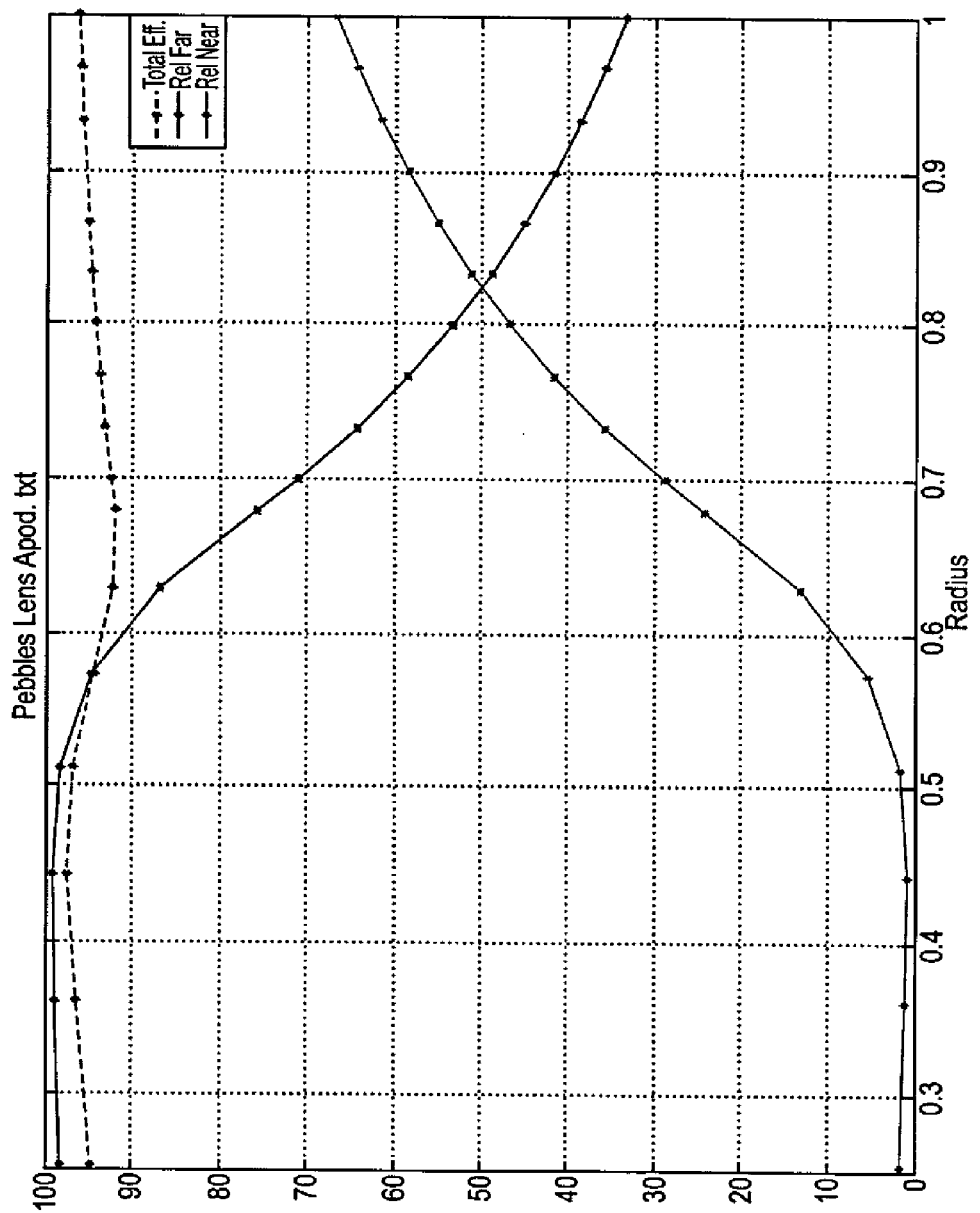
FIG. 9 is a simplified graph showing light intensities at different radiuses for a lens with an apodized surface function according to FIG. 8.

Reference is now made to FIG. 9, which is a simplified graph illustrating the relative energy distribution between two focal planes achieved by the apodized surface of FIG. 8.

Figure 10:
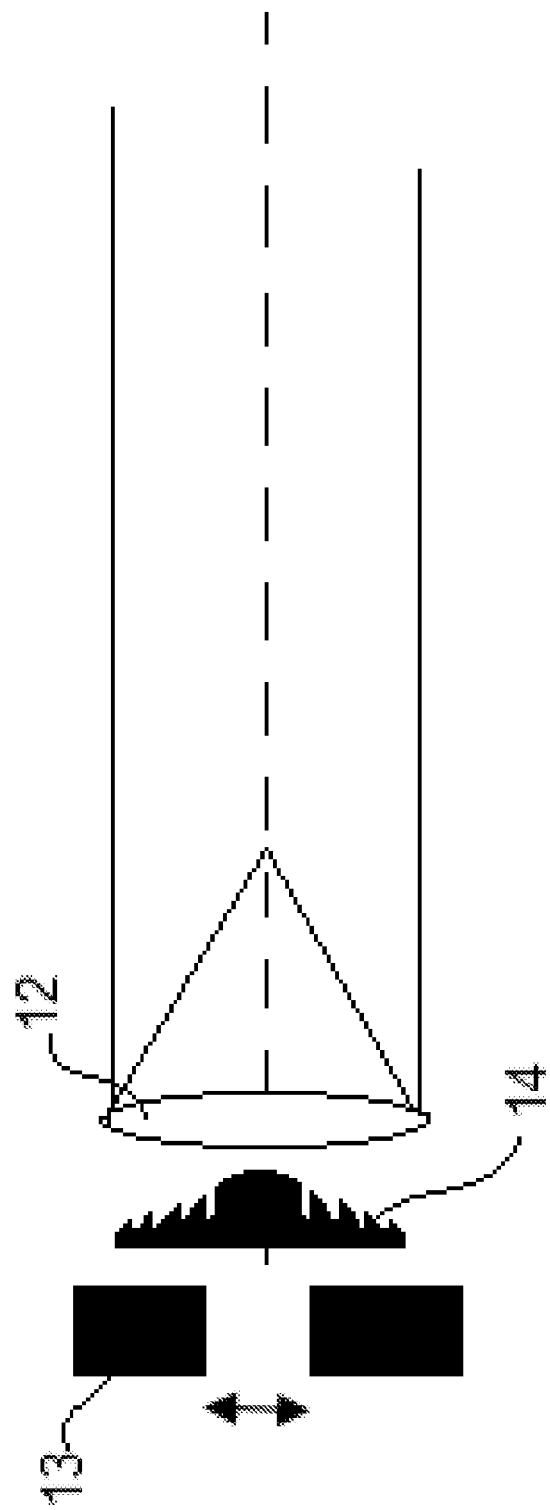
FIG. 10 is a simplified schematic diagram showing how a shutter can be placed in relation to an apodized diffractive lens to vary the amounts of light falling on the different regions of the lens according to an embodiment of the present invention.

Reference is now made to FIG. 10, which illustrates an apodized multi focal setup comprising a refractive lens 12, an apodized lens 14 and a shutter 13. By changing the aperture of the shutter, the light energy can be distributed dynamically over the different regions of the lens 14. Thus light can be directed towards the near proximity for depth sensing of objects at near proximities. Alternatively, by movement of the shutter, light can be directed towards a different region of the lens for the more distant foci. The apodized lens has variable heights of the diffractive teeth or steps as one traverses the surface of the lens. The varying heights are one way of providing the apodizing function to the surface of the lens.

A further embodiment may be provided as a controllable beam expander.

The terms "comprises", "comprising", "includes", "including", "having" and their conjugates mean "including but not limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An optical sensing device comprising:
   a light source;
   a multi-focal lens having a plurality of foci configured to focus light from the light source into a space at a plurality of focal points related to the plurality of foci, wherein the multi-focal lens comprises a lens surface shaped to provide an apodized surface function;
   a sensor configured to sense focused light of the light source reflected from an object in the space to sense the object or features of the object; and
   an adjustable shutter placed in relation to the multi-focal lens configured to be altered for controlling amounts of light from the light source falling over different regions of the shaped surface of the multi-focal lens to vary amounts of energy of light at the plurality of focal points.

2. The optical sensing device of claim 1, further comprising a light structuring unit for adding structure to light of the light source, for recognition by the optical sensing device.

3. The optical sensing device of claim 1, wherein the space is a three-dimensional space and the plurality of foci comprises foci at two different distances.

4. The optical sensing device of claim 3, wherein one of the plurality of foci is a focus at infinity.

5. The optical sensing device of claim 2, wherein the light structuring unit is one member of the group consisting of a diffractive pattern generator, an amplitude mask, a phase mask, and a patterned film.

6. The optical sensing device of claim 1, wherein the multi-focal lens is a diffractive lens having diffractive steps, each step having a height, and wherein respective heights are varied over the surface to provide the apodized surface function.

7. The optical sensing device of claim 1, wherein the adjustable shutter is altered to provide a beam expansion setup of the optical sensing device.

8. An optical sensing method comprising:
   shining light from a light source on a multi-focal lens having a plurality of foci configured to focus light from the light source into a space at a plurality of focal points related to the plurality of foci, wherein the multi-focal lens comprises a lens surface shaped to provide an apodized surface function;
   sensing focused light of the light source reflected from an object in the space to sense the object or features of the object; and
   controlling amounts of light from the light source falling over different regions of the shaped surface of the multi-focal lens to vary amounts of energy of light at the plurality of focal points.

9. The optical sensing method of claim 8, further comprising adding structure to light of the light source for sensing the focused light of the light source reflected from the object.

10. The optical sensing method of claim 8, wherein the multi-focal lens is a diffractive lens having diffractive steps, each step having a height, and wherein respective heights are varied over the surface to provide the apodized surface function.

11. The optical sensing method of claim 8, further comprising
  directing light from the light source sequentially between the different regions of the shaped surface.

12. The optical sensing method of claim 8, wherein one of the plurality of foci is at infinity.

* * * * *